United States Patent [19]

Müller et al.

[11] Patent Number: 5,414,008
[45] Date of Patent: May 9, 1995

[54] IMIDAZOLYL-SUBSTITUTED PHENYLPROPIONIC AND CINNAMIC ACID DERIVATIVES

[75] Inventors: Ulrich E. Müller; Jürgen Dressel; Peter Fey, all of Wuppertal; Rudolf H. Hanko, Duesseldorf; Walter Hübsch, Wuppertal; Thomas Krämer, Wuppertal; Matthias Müller-Gliemann, Solingen; Martin Beuck, Erkrath; Stanislav Kazda, Wuppertal; Andreas Knorr, Erkrath; Johannes-Peter Stasch, Wuppertal; Stefan Wohlfeil, Hilden, all of Germany

[73] Assignee: Bayer Aktiengesellschaft, Leverkusen, Germany

[21] Appl. No.: 80,854

[22] Filed: Jun. 21, 1993

[30] Foreign Application Priority Data

Jun. 26, 1992 [DE] Germany .................. 42 20 983.8

[51] Int. Cl.[6] .................... A61K 31/415; C07D 403/10
[52] U.S. Cl. ..................... 514/381; 548/252; 548/253; 548/254
[58] Field of Search ............... 514/381; 548/252, 253, 548/254

[56] References Cited

U.S. PATENT DOCUMENTS

| | | | |
|---|---|---|---|
| 4,355,040 | 10/1982 | Furukawa et al. | 424/273 R |
| 4,946,841 | 8/1990 | Baader et al. | 514/247 |
| 5,168,956 | 12/1992 | Namioka | 180/248 |
| 5,183,810 | 2/1993 | Greenlee et al. | 514/63 |

FOREIGN PATENT DOCUMENTS

| | | |
|---|---|---|
| 324377 | 1/1989 | European Pat. Off. |
| 399731 | 5/1990 | European Pat. Off. |
| 399732 | 5/1990 | European Pat. Off. |
| 407102 | 6/1990 | European Pat. Off. |

OTHER PUBLICATIONS

Journal of the American Chemical Society/99.9/Apr. 27, 1977, "Inductive Enhancement of Aryl Participation", Joseph Lambert, et al. pp. 3059–3067.
The Journal of Cell Biology, vol. 50, 1971, pp. 172–186, "The Smooth Muscle Cell", Russell Ross.
Russian Chemical Reviews, Usepekhi Khimii, Jan. 1963, pp. 1–20, "Mechanisms of the Hydrolysis of Aromatic Sulphonyl Chlorides . . . ".
J. March, Advanced Organic Chemistry, Second Edition, pp. 836–841. (1977).
N. Leo Benoiton, et al. Int. J. Peptide Protein Res. 17, 1981, pp. 197–204.
Journal of Biological Chemistry, Frerman et al., J. Biol. Chem. 258, pp. 7087–7093. (1983).
Sheehan, Ledis/Total Synthesis of Etamycin, 1973, pp. 875–879.

*Primary Examiner*—Patricia L. Morris
*Attorney, Agent, or Firm*—Sprung Horn Kramer & Woods

[57] ABSTRACT

Imidazolyl-substituted phenylpropionic and cinnamic acid derivatives are prepared by reacting appropriate benzyl compounds with imidazoles and optionally varying the substituents. The imidazolyl-substituted phenylpropionic and cinnamic acid derivatives can be used as active compounds in medicaments, in particular in the treatment of arterial hypertension and atherosclerosis.

8 Claims, No Drawings

IMIDAZOLYL-SUBSTITUTED PHENYLPROPIONIC AND CINNAMIC ACID DERIVATIVES

The invention relates to imidazolyl-substituted phenyl-propionic and cinnamic acid derivatives, a process for their preparation and their use in medicaments, in particular as hypotensive and antiatherosclerotic agents.

It is known that renin, a proteolytic enzyme, eliminates the decapeptide angiotensin I from angiotensin in vivo, and the angiotensin I is in turn degraded in the lung, the kidneys or other tissues to give the hypertensive octapeptide angiotensin II. The various effects of angiotensin II, such as, for example, vasoconstriction, $Na^+$ retention in the kidney, aldosterone release in the adrenal gland and increase in tone of the synthetic nervous system act synergistically in the sense of a blood pressure increase.

Moreover, angiotensin II has the property of promoting the growth and the replication of cells such as, for example, cardiac muscle cells and smooth muscle cells, these growing and proliferating in an increased manner in various disease states (for example hypertension, atherosclerosis and cardiac insufficiency).

Apart from inhibition of renin activity, a possible starting point for intervention in the renin-angiotensin system (RAS) is the inhibition of the activity of angiotensin-converting enzyme (ACE) and the blockade of angiotensin II receptors.

Heterocyclic compounds having AII antagonistic action are additionally known from the publications EP 407,102, EP 399,731, EP 399,732, EP 324,347 and EP 253,310.

Imidazole benzyl derivatives which have a substituted vinyl group on the phenyl ring and which have a peptic ulcer-inhibitory action are also described in the publications JP 02 053,779 and JP 62 039,576.

The present invention relates to imidazolyl-substituted phenylpropionic and cinnamic acid derivatives of the general formula ( I )

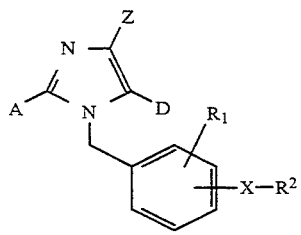

in which
A represents straight-chain or branched alkyl or alkenyl each having up to 8 carbon atoms, or represents cycloalkyl having 3 to 8 carbon atoms,
Z represents hydrogen, halogen or perfluoroalkyl having up to 5 carbon atoms,
D represents a group of the formula $-CH_2-OR^3$ or $-CO-R^4$,
in which
$R^3$ denotes hydrogen or straight-chain or branched alkyl having up to 8 carbon atoms,
$R^4$ denotes hydrogen, hydroxyl or straight-chain chain or branched alkoxy having up to 8 carbon atoms, X represents a group of the formula

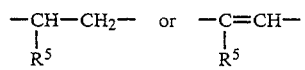

in which
$R^5$ denotes cycloalkyl having 3 to 8 carbon atoms, or denotes phenyl, or denotes straight-chain or branched alkyl having up to 8 carbon atoms, which is optionally substituted by phenyl or cycloalkyl having 3 to 8 carbon atoms,
$R^1$ represents hydrogen, halogen, nitro, hydroxyl, tri-fluoromethyl, trifluoromethoxy, straight-chain or branched alkyl, alkoxy or alkoxycarbonyl each having up to 6 carbon atoms, or cyano or carboxyl,
$R^2$ represents carboxyl, straight-chain or branched alkoxycarbonyl having up to 8 carbon atoms, or azido, or represents a radical of the formula $-NR^6R^7$, $-CO-NR^8R^9$ or

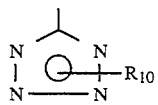

in which
$R^6$, $R^7$, $R^8$ and $R^9$ are identical or different and denote hydrogen, straight-chain or branched alkyl having up to 8 carbon atoms, benzyl or phenyl,
or
$R^6$ and $R^8$ have the abovementioned meaning
and
$R^7$ and/or $R^9$ denote a group of the formula $-SO_2R^{11}$ or $-CO-R^{12}$,
in which
$R^{11}$ denotes trifluoromethyl or straight-chain or branched alkyl having up to 8 carbon atoms, which is optionally substituted by phenyl which can in turn be substituted by straight-chain or branched alkyl having up to 6 carbon atoms, or denotes phenyl which is optionally substituted by straight-chain or branched alkyl having up to 6 carbon atoms,
$R^{12}$ denotes straight-chain or branched alkyl having up to 8 carbon atoms, or benzyl or phenyl which is optionally substituted by straight-chain or branched alkyl having up to 6 carbon atoms,
or
$R^8$ denotes hydrogen
and
$R^9$ denotes the group of the formula

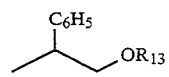

in which
$R^{13}$ denotes hydrogen or straight-chain or branched alkyl having up to 6 carbon atoms,
$R^{10}$ denotes hydrogen, straight-chain or branched alkyl having up to 6 carbon atoms or the tri-phenylmethyl group and their salts.

The compounds of the general formula (I) according to the invention can also be present in the form of their salts. In general, salts with organic or inorganic bases or acids may be mentioned here.

In the context of the present invention, physiologically acceptable salts are preferred. Physiologically acceptable salts of the imidazolyl-substituted phenylpropionic and -cinnamic acid derivatives can be salts of the substances according to the invention with mineral acids, carboxylic acids or sulphonic acids. Particularly preferred salts are, for example, those with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Physiologically acceptable salts can also be metal or ammonia salts of the compounds according to the invention which have a free carboxyl group. Those particularly preferred are, for example, sodium, potassium, magnesium or calcium salts, and also ammonium zalts which are derived from ammonia, or organic amines such as, for example, ethylamine, di- or trithylamine, di- or triethanolmine, dicylohexylamine, dimethylaminoethanol, arginine, lysine or ethylenediamine.

The compounds according to the invention can exist in stereoisomeric forms which either behave as image and mirror image (cnantiomers), or which do not behave as image and mirro image (diastereomers). The invention relates both to the enantiomers and diastereomers or to their respective misxutes. Like the diastereomers, the racemic forms can be separated into the stereoisomericfally uniform constituents in a known manner [cf. E. L. Eliel, Stereochemistry of Carbon Compounds, McGraw Hill, 1962].

Hyaroxyl protective groups in the context of the above-mentioned definition in general represent a protective group from teh series consistine of: trimethylsilyl, triethylsilyl, triisopropylsilyl, tert-butyl-dimethylsilyl, tert-butyldiphenylsilyl, trimethylsilylethoxy-carbonyl, benzyl, tripenylmethyl(trityl), monomethoxy-trityl (MMTr), dimethoxytritryl. (DMTr), benzyloxy-carbonyl, 2-nitrobenzyl, 4-nitrobenzyl, 2-nitro-benzyloxycarbonyl, 4-nitrobenzyloxycarbonyl, tert-butoxycarbonyl, 4-methoxybenzyl, 4methoxybenzyl-oxycarbonyl, formyl, acetyl, trichloroacetyl, 2,2,2-trichloroethoxycarbonyl, 2,4-dimethoxybenzyl, 2,4-dimethoxybenzyloxycarbonyl, methoxymethyl, methylthiomethyl, methoxyethoxymethyl, [2-(trimethylsilyl)ethoxy]-methyl, -(methylthiomethoxy)ethoxycarbonyl, tetrahydropyranyl, benzoyl, 4-methylbenzoyl, 4-nitrobenzoyl, 4-fluorobenzoyl, 4-chlorobenzoyl or 4-methoxybenzoyl. Acetyl is preferred.

Preferred compounds of the general formula (I) are those
in which
A represents straight-chain or branched alkyl or alkenyl each having up to 6 carbon atoms, or represents cyclopropyl, cyclobutyl, cyclopentyl, cyclohexyl or cycloheptyl,
Z represents hydrogen, fluorine, chlorine, bromine or perfluoroalkyl having up to 4 carbon atoms,
D represents a group of the formula -CH$_2$OR$^3$ or -CO-R$^4$,
in which
R$^3$ denotes hydrogen or straight-chain or branched alkyl having up to 6 carbon atoms,
R$^4$ denotes hydrogen, hydroxyl or straight-chain or branched alkoxy having up to 6 carbon atoms,
X represents a group of the formula $$-\underset{R^5}{CH}-CH_2- \quad \text{or} \quad -\underset{R^5}{C}=CH-$$

in which
R$^5$ denotes cyclopropyl, cyclopentyl, cyclohexyl, cycloheptyl or phenyl, or denotes straight-chain or branched alkyl having up to 6 carbon atoms, which is substituted by phenyl, cyclopropyl, cyclopentyl, cyclohexyl or cycloheptyl,
represents hydrogen, fluorine, chlorine, bromine, trifluoromethyl, carboxyl or straight-chain or branched alkyl, alkoxy or alkoxycarbonyl each having up to 4 carbon atoms,
R$^2$ represents carboxyl, straight-chain or branched alkoxycarbonyl having up to 6 carbon atoms, or azido, or represents a radical of the formula -NR$^6$R$^7$, -CO-NR$^8$R$^9$ or in which
R$^6$, R$^7$, R$^8$ and R$^9$ are identical or different and denote hydrogen, straight-chain or branched alkyl having up to carbon atoms, benzyl or phenyl,
or
R$^6$ and R$^8$ have the abovementioned meaning
and
R$^7$ and/or R$^9$ denote a group of the formula -SO$_2$R$^{11}$ or -CO-R$^{12}$
in which
R$^{11}$ denotes trifluoromethyl or straight-chain or branched alkyl having up to 6 carbon atoms, which is optionally substituted by phenyl which can in turn be substituted by straight-chain or branched alkyl having up to 4 carbon atoms, or denotes phenyl which is optionally substituted by straight-chain or branched alkyl having up to 4 carbon atoms,
R$^{12}$ denotes straight-chain or branched alkyl up to 6 carbon atoms, phenyl, benzyl or tolyl
or
R$^8$ denotes hydrogen
and
R$^9$ denotes the group of the formula in which
R$^{13}$ denotes hydrogen or straight-chain or branched alkyl having up to 4 carbon atoms
R$^{10}$ denotes hydrogen, straight-chain or branched alkyl having up to 4 carbon atoms or the triphenylmethyl group and their salts.

Particularly preferred compounds of the general formula (I) are those in which
A represents straight-chain or branched alkyl or alkenyl each having up to 4 carbon atoms, or represents cyclopropyl, cyclopentyl or cyclohexyl,
Z represents hydrogen, fluorine, chlorine or perfluoroalkyl having up to 2 carbon atoms, D represents a group of the formula -CH$_2$OR$^3$ or -CO-R$^4$, in which R$^3$ denotes hydrogen or straight-chain or branched alkyl having up to 4 carbon atoms, R$^4$ denotes hydrogen, hydroxyl or straight-chain or branched alkoxy having up to 4 carbon atoms, X represents a group of the formula

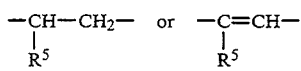

in which

R$^5$ denotes cyclopentyl, cyclohexyl or phenyl, or denotes straight-chain or branched alkyl having up to 4 carbon atoms, which is optionally substituted by phenyl, cyclopentyl or cyclohexyl, R$^1$ represents hydrogen, fluorine, chlorine, bromine, trifluoromethyl, trifluoromethoxy or methyl, represents carboxyl, straight-chain or branched alkoxycarbonyl having up to 4 carbon atoms or azido, or represents a radical of the formula -NR$^6$R$^7$, -CO-NR$^8$R$^9$ or

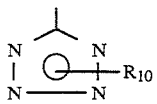

in which

R$^6$, R$^7$, R$^8$ and R$^9$ are identical or different and denote hydrogen, straight-chain or branched alkyl having up to 4 carbon atoms, benzyl or phenyl, or R$^6$ and R$^8$ have the abovementioned meaning, and R$^7$ and/or R$^9$ denote a group of the formula -SO$_2$-R$^{11}$ or -CO-R$^{12}$ in which R$^{11}$ denotes trifluoromethyl or straight-chain or branched alkyl having up to 4 carbon atoms, which can optionally be substituted by phenyl or tolyl, or denotes phenyl or tolyl, R$^{12}$ denotes straight-chain or branched alkyl having up to 4 carbon atoms, or benzyl, phenyl or tolyl, or R$^8$ denotes hydrogen and R$^9$ denotes the group of the formula

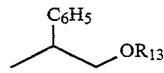

in which

R$^{13}$ denotes hydrogen, methyl or ethyl,

R$^{10}$ denotes hydrogen, methyl or the triphenylmethyl and their salts.

A process for the preparation of the compounds of the general formula (I) according to the invention has additionally been found, characterised in that compounds of the general formula (II)

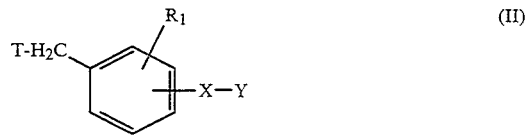

in which

R$^1$ and X have the abovementioned meaning,

T represents a typical leaving group such as, for example, chlorine, bromine, iodine, tosylate or mesylate, preferably bromine, and Y represents straight-chain or branched (C$_1$-C$_4$)-alkoxy-carbonyl or the triphenylmethyl-tetrazol-1-yl group, are reacted first with imidazoles of the general formula (III)

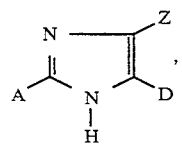

in which

A, Z and D have the abovementioned meaning, in inert solvents, if appropriate in the presence of a base and if appropriate under a protective gas atmosphere, to give compounds of the general formula (IV)

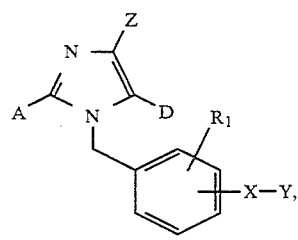

in which

A, Z, D, R$^1$ and X and Y have the abovementioned meaning, and in the case of the acids (R$^2$=CO$_2$H), the esters are hydrolysed, and in the case of the amines, amides and sulphonamides, reacted with compounds of the general formula (V)

in which

R$^{14}$ and R$^{15}$ have the respective scope of meaning of R$^6$, R$^7$, R$^8$ and R$^9$, if appropriate in the presence of a base and/or of an auxiliary, for example of a dehydrating agent, in inert solvents, and in the case of the free tetrazole, the trityl group is removed with acids, preferably with trifluoroacetic acid or hydrochloric acid in dioxane, and if appropriate the substituents A, Z, D and R$^1$ are introduced or converted into other groups by customary methods, for example by reduction, oxidation, alkylation or hydrolysis, and if appropriate the isomers are separated, and in the case of the preparation of the salts reacted with an appropriate base or acid, and in the case of the esters, starting from the activated carboxylic acids, reacted with the appropriate alkoxides.

The process according to the invention can be illustrated by way of example by the following reaction scheme:

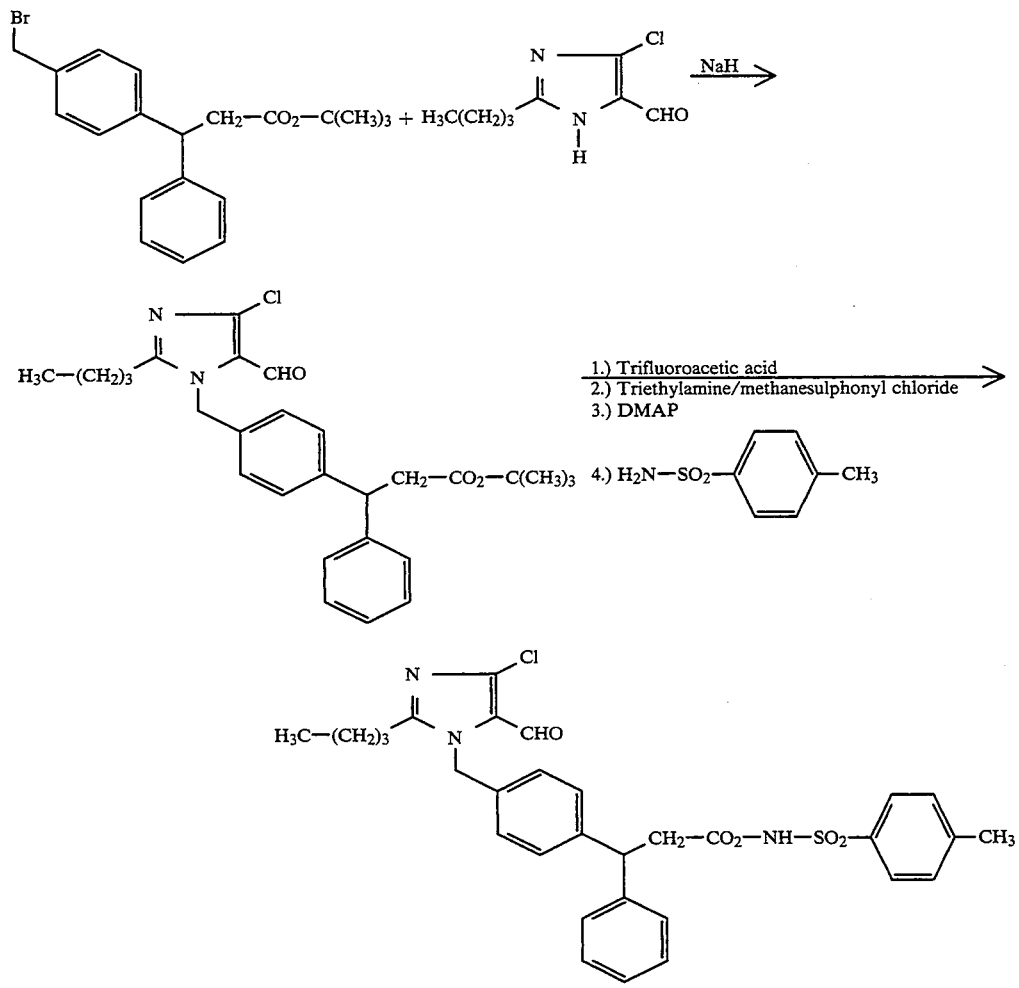

ple, barium hydroxide, alkali metal carbonates such as sodium carbonate or potassium carbonate, alkaline earth metal carbonates such as calcium carbonate, or alkali metal or alkaline earth metal alkoxides such as sodium methoxide or potassium methoxide, sodium ethoxide or potassium ethoxide or potassium tert-butoxide, or organic amines (trialkyl($C_1$—$C_6$)amines) such as triethylamine, or-heterocycles such as 1,4-diazabicyclo[2.2.2]octane (DABCO), 1,8-diazabicyclo[5.4.0]undec-7-ene (DBU), pyridine, diaminopyridine, methylpiperidine or morpholine. It is also possible to employ alkali metals such as sodium or their hydrides such as sodium hydride as bases. Sodium hydride, potassiumcarbonate, triethylamine, pyridine and potassium tert-butoxide are preferred.

Suitable solvents for the process are the customary organic solvents which do not change under the reaction conditions. These preferably include ethers such as diethyl ether, dioxane, tetrahydrofuran, glycol dimethyl ether, or hydrocarbons such as benzene, toluene, xylene, hexane, cyclohexane, or mineral oil fractions, or halogenohydrocarbons such as dichloromethane, trichloromethane, tetrachloromethane, dichloroethylene, trichloroethylene or chlorobenzene, or ethyl acetate, triethylamine, pyridine, dimethyl sulphoxide, dimethylformamide, hexamethylphosphoramide, acetonitrile, acetone or nitromethane. It is also possible to use mixtures of the solvents mentioned. Dimethylformamide and tetrahydrofuran are preferred.

The bases employed for the process according to the invention can in general be inorganic or organic bases. These preferably include alkali metal hydroxides such as, for example, sodium hydroxide or potassium hydroxide, alkaline earth metal hydroxides such as, for exam- In general the base is employed in an amount from 0.05 to 10 mol, preferably from 1 mol to 2 mol, relative to 1 mol of the compound of the formula (III).

The process according to the invention is in general carried out in a temperature range from —30° C. to +100° C., preferably from —10° C. to +60° C., The process according to the invention is in general carried out at normal pres sure. However, it is also possible to carry out the process at elevated pressure or at reduced pressure (for example in a range from 0.5 to 5 bar ) .

Suitable bases for the hydrolysis are the customary inorganic bases. These preferably include alkali metal hydroxides or alkaline earth metal hydroxides such as, for example, lithium hydroxide, sodium hydroxide, potassium hydroxide or barium hydroxide, or alkali metal carbonates such as sodium carbonate or potassium carbonate or sodium hydrogen carbonate, or alkali metal alkoxides such as sodium methoxide, sodium ethoxide, potassium methoxide, potassium ethoxide or potassium tert-butoxide. Lithium hydroxide, sodium hydroxide or potassium hydroxide is particularly preferably employed.

Suitable solvents for the hydrolysis are water or the organic solvents customary for hydrolysis. These preferably include alcohols such as methanol, ethanol, propanol, isopropanol or butanol, or ethers such as tetrahydrofuran or dioxane, or dimethylformamide or dimethyl sulphoxide. Alcohols such as methanol, etahanoi, propanol or isopropanol are particularly preferablyused. It is also possible to employ mixtures of the solvents mentioned.

The hydrolysis is preferably carried out using acids such as, for example, trifluoroacetic acid, acetic acid, hydrochloric acid, hydrochloric acid/dioxane, hydrobromic acid, methanesulphonic acid, sulphuric acid orperchloric acid, particularly preferably using trifluoroacetic acid or hydrochloric acid/dioxane.

The hydrolysis is in general carried out in a. temperature range from 0° C. to +100° C., preferably from +20° C. to +80° C.

In general, the hydrolysis is carried out at normal pressure. However, it is also possible to work at reduced pressure or at elevated pressure (for example from 0.5 to 5 bar ).

When carrying out the hydrolysis, the base is in general employed in an amount from 1 to 3 mol, preferably from 1 to 1.5 mol, relative to 1 mol of the ester. Molar amounts of the reactants are particularly preferably used.

When carrying out the reaction, the carboxylates of the compounds according to the invention are formed in the first step as intermediates which can be isolated. The acids according to the invention are obtained by treating the carboxylates with customary inorganic acids. These preferably include acids such as, for example, hydrochloric acid, hydrobromic acid, sulphuric acid, phosphoric acid or trifluoroacetic acid. It has also proven advantageous in this case in the preparation of the carboxylic acids to acidify the basic reaction mixture from the hydrolysis in a second step without isolation of the carboxylates. The acids can then be isolated in a customary manner.

The amidation and the sulphonamidation of the compounds of the general formula (IV) is in general carried out in one of the abovementioned solvents, preferably in tetrahydrofuran or dichloromethane.

The amidation or sulphonamidation can proceed starting from the compounds of the general formula (IV), if appropriate via the activated stage of the acid halides or mixed anhydrides, which can be prepared from the corresponding acids by reaction with thionyl chloride, phosphorus trichloride, phosphorus pentachloride, phosphorus tribromide or-oxalyl chloride, or methanesulphonyl chloride.

The amidation or sulphonamidation is in general carried out in a temperature range from —50° C. to +80° C., preferably from —30° C. to +20° C., and at normal pressure.

In addition to the abovementioned bases, suitable bases for this reaction are preferably triethylamine and/or dimethylaminopyridine, DBU or DABCO.

The base is employed in an amount from 0.5 mol to 10 mol, preferably from 1 mol to 5 mol, relative to 1 mol of the compounds of the general formula (V).

Acid-binding agents which can be employed for the amidation or sulphonamidation are alkali metal or alkaline earth metal carbonates such as sodium carbonate, potassium carbonate, alkali metal or alkaline earth metal hydroxides such as, for example, sodium hydroxide or potassium hydroxide, or organic bases such as pyridine, triethylamine, N-methylpiperidine, or bicyclic amidines such as 1,5-diazabicyclo[3.4.0]-non-5-ene (DBN) or 1,5-diazabicyclo[3.4.0]undec-5-ene (DBU). Triethylamine is preferred.

Suitable dehydrating reagents are carbodiimides such as, for example, diisopropylcarbodiimide, dicyclohexylcarbodiimide or N-(3-dimethylaminopropyl ) -N-ethylcarbodiimide hydrochloride or carbonyl compounds such as carbonyldiimidazole or 1,2-oxazolium compounds such as 2-ethyl-5-phenyl-1,2-oxazolium-3-sulphonate or propanephosphonic anhydride or isobutyl chloroformate, or benzotriazolyloxy-tris-( dimethylamino ) phosphonium hexafluorophosphate or diphenyl phosphoramidate or methanesulphonyl chloride, if appropriate in the presence of bases such as triethylamine or N-ethylmorpholine or N-methylpiperidine or dicyclohexylcarbodiimide and N-hydroxysuccinimide [cf. J. C. Sheehan, S. L.Ledis, J. Am. Chem. Soc. 95, 875 (1973); F. E., Freeman et. al., J. Biol. Chem. 225, 507 (1982) and N. B. Benoton, K. Kluroda, Int. Pept. Prot. Res. 13, 403 (1979), 17, 187 (1981)].

The acid-binding agents and dehydrating reagents are in general employed in an amount from 0.5 to 3 mol, preferably from 1 to 1.5 mol, relative to 1 mol of tohe corresponding carboxylic acids.

The abovementioned derivatisation of the substituents A, B, D and $R^1$ is in general carried out by methods known from the literature, where the reduction of aldehydes or alkoxycarbonyl compounds to alcohols (a), the reduction of double bonds (b) and the alkylation (c) will be illustrated by way of example by the following:

a) The reduction of alkoxycarbonyl compounds or aldehydes to the corresponding alcohols is in general carried out using hydrides, such as lithium aluminiumhydride or sodium borohydride, preferably using lithium aluminium hydride in inert solvents such as ethers, hydrocarbons or alcohols or mixtures thereof, preferably in ethers such as, for example, diethyl ether, tetrahydrofuran or dioxane, or alcohols such as ethanol, in the case of the aldehydes preferably using sodium borohydride in ethanol, in a temperature range from 0° C. to +150° C., preferably from +20° C. to +100° C., at normal pressure.

The reduction of a double bond is in general carried out by hydrogenation with hydrogen in the presence of a catalyst such as, for example, platinum or platinum oxides, rhodium, ruthenium, chlorotris(tri-phenylphospine)rhodium, or palladium on animal charcoal, preferably using palladium on animal charcoal in a temperature range from 0° C. to +150° C., preferably from +25° C. to +100° C.

b) Suitable solvents for the hydrogenation are protic solvents such as, for example, methanol, ethanol, and/or aprotic solvents such as, for example, tetrahydrofuran, toluene, dimethylformamide, methylene chloride, dioxane or ethyl acetate.

The hydrogenation is carried out at pressure from 1 to 300 atm, preferably at 1 to 20 atm.

c) The alkylation is in general carried out in one of the abovementioned solvents using alkylating agents such as, for example, ($C_1$–$C_8$)-alkyl halides, sulphonic acid esters or substituted or unsubstituted ($C_1$-$C_6$)-dialkyl or ($C_1$-$C_{10}$)-diaryl sulphates, preferably methyl iodide, p-toluenesulphonic esters or dimethyl sulphate.

The compounds of the general formula (II) are new and can be prepared by first converting, in the case in which the radical X represents the

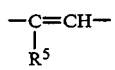

group, compounds of the general formula

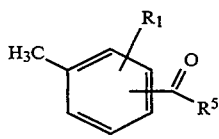

(VI)

in which $R^1$ and $R^5$ have the abovementioned meaning, by reduction according to customary methods, preferably us ing sodium hydride, in one of the abovementioned solvents, preferably in toluene, and by subsequent esterification, into the compounds of the general formula (VII)

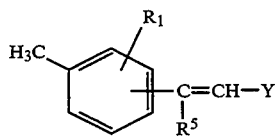

(VII)

in which $R^1$, $R^5$ and Y have the abovementioned meaning, and in a second step carrying out a bromination of the methyl group, if appropriate in the presence of a catalyst, and in the case in which X represents the

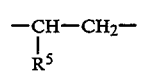

group, either reducing compounds of the general formula (VII) according to customary methods or first reducing compounds of the general formula (VI) in a Grignard reaction, for example using ($C_1$–$C_4$)-alkylmagnesium halides, preferably bromides, and simultaneously introducing the radical $R^2$ and then carrying out the bromination as described above, and if appropriate varying the substituent $R^1$ as described above in the stages of the general formula (VI) or (VII).

The reduction is carried out either by hydrogen in water or in inert organic solvents such as alcohols, ethers, or halogenohydrocarbons, or mixtures thereof, using catalysts such as Raney nickel, palladium, palladium on animal charcoal, or platinum, or else using hydrides in inert solvents, if appropriate in the presence of a catalyst.

The reduction of the double bond is carried out in a temperature range from 0° C. to +40° C., preferably at +20° C. and at a pressure of 1 bar.

The esterification is carried out in one of the abovementioned solvents, preferably toluene or tetrahydrofuran, after the prior activation of the corresponding carboxylic acid already described above, preferably via the carbonyl chlorides, and subsequent reaction with the appropriate alkoxides, in a temperature range from 0° C. to +60° C., preferably at +10° C. to +35° C. and at normal pressure.

The removal of the magnesium halide group is carried out by the method customary for Grignard reactions using aqueous ammonium chloride solution [cf. J. March, Advanced Organic Chemistry, Second Edition p. 836].

The bromination is in general carried out in a temperature range from +40° C. to +100° C., preferably from +60° C. to +90° C. and at normal pressure. It is carried out in one of the abovementioned solvents, preferably using carbon tetrachloride, and using N-bromosuccinimide.

A suitable starter (catalyst) for the bromination is, for example, azobisisobutyronitrile, dibenzoyl peroxide, preferably azobisisobutyronitrile, the starter being employed in an amount from 0.01 to 0.1 mol, preferably from 0.01 to 0.05 mol, relative to 1 mol of the compound of the general formula (VI).

The compounds of the general formula (VI) are in the main known or can be prepared by customary methods.

The compounds of the general formula (VIII) are new and can be prepared, for example, as described above.

The compounds of the general formula (I I I) are known per se or can be prepar, ed by customary methods [cf., for example, Beilstein 25, 163; 23, 45; U.S. Pat. No. 4,355,040].

The compounds of the general formula (IV) are new and can be prepared as described above, for example.

The compounds of the general formula (V) are known [cf., for example, Beilstein 11/104, R.V. Vitzgert, Uspekhi, Khimii 32, 3 (1963); Russian Chem. Rev. 32, 1 (1969); Beilstein 4, 87 ].

The compounds of the general formula (I) according to the invention exhibit an unforeseeable, useful range of pharmacological action.

The compounds according to the invention have a specific A II-antagonistic action, since they competitively inhibit the binding. of angiotensin II to the receptors. They suppress the vasoconstrictory and aldosterone secretion-stimulating effects of angiotensin II. They moreover inhibit the proliferation of smooth muscle cells.

They can therefore be employed in medicaments for the treatment of arterial hypertension and atherosclerosis. They can moreover be employed for the treatment of coronaryheart diseases, cardiac insufficiency, disorders of the brain function, ischemic cerebral diseases, peripheral circulatorydisorders, functional disorders of the kidney and adrenal gland, bronchospastic diseases and respiratory tract diseases having a vascular component, sodium retention and oedemas.

Investigation of the inhibition of the contraction induced by gonists

Rabbits of either sex are stunned by a blow to the back of the head and bled out, or in some cases anaesthetized with Nembutal (about 60-80 mg/kg i.v.) and sacrificed by opening the thorax. The thorax aorta is removed, freed from adhering connective tissue, divided into ring segments 1.5 mm wide and individually transferred under an initial loading of about 3.5 g to 10 ml organ baths containing Krebs-Henseleit nutrient solution, which is temperature-controlled at 37° C. and aerated with 95% $O_2$/5% $CO_2$, of the following composition: 119 mmol/l of NaCl; 2.5mmol/l of $CaCl_2 \times 2H_2O$; 1.2 mmol/l of $KH_2PO_4$; 10mmol/l of glucose; 4.8 mmol/l of KCl; 1.4 mmol/l of $MgSO_4 \times H_2O$ and 25 mmol/l of $NaHCO_3$.

The contractions are detected isometrically by Statham UC2 cells by means of bridge amplifiers (ifd Milheim or DSM Aalen) and digitalised and assessed by means of A/D converters (System 570, Keithley Munich). Agonist dose response curves (DRC) are plotted hourly. With each DRC, 3 or 4 individual concentrations are applied to the baths at a 4 min interval. After the end of the DRC and subsequent washing-out cycles (16 times in each case about 5 sec/min with the above-mentioned nutrient solution), a 28-minute rest or incubation phase follows, during which the contractions as a rule reach the staring value again.

The height of the 3rd DRC, in a normal case, is used as a reference variable for the assessment of the test substance to be investigated in further runs, which is applied to the baths in the following DRCs in increasing doses in each case at the start of the incubation period. Each aorta ring is in this case stimulated for the whole day, always with the same agonist.

| Agonists and their standard concentrations (application volume per individual dose = 100 µl): | | |
|---|---|---|
| KCl | 22.7; 32.7; 42.7; 52.7 | mmol/l |
| 1-Noradrenaline | $3 \times 10^{-9}$; $3 \times 10^{-8}$; $3 \times 10^{-7}$; $3 \times 10^{-6}$ | g/ml |
| Serotonin | $10^{-8}$; $10^{-7}$; $10^{-6}$; $10^{-5}$ | g/ml |
| B-HT 920 | $10^{-7}$; $10^{-6}$; $10^{-5}$; | g/ml |
| Methoxamine | $10^{-7}$; $10^{-6}$; $10^{-5}$; | g/ml |
| Angiotensin II | $3 \times 10^{-9}$; $10^{-8}$; $3 \times 10^{-8}$; $10^{-7}$ | g/ml |

For the calculation of the $IC_{50}$ (concentration at which the substance to be investigated causes a 50% inhibition), the effect is in each case based on the 3rd =submaximal agonist concentration.

The compounds according to the invention inhibit the contraction induced of the isolated rabbit aorta induced by angiotensin II in a dose-dependent manner. The contraction induced by potassium depolarisation or other agonists was not inhibited or only weakly inhibited at high concentrations.

TABLE A

Inhibition of vascular contraction in isolated rabbit aorta rings in vitro
$IC_{50}$ (g/ml) against contractions induced by AII

| Ex. No.: | $IC_{50}$ [nM] |
|---|---|
| 20 | 360 |
| 30 | 580 |
| 31 | 360 |
| 35 | 650 |

Blood pressure measurements on the anqiotensin II-infused rat.

Male Wistar rats (Moellegaard, Copenhagen, Denmark) having a body weight of 300-350 g are anaesthetized with thiopental (100 mg/kg i.p.). After tracheotomy, a catheter for blood pressure measurement is inserted in the femoral artery and a catheter for angiotensin II infusion and a catheter for substance administration are inserted in the femoral veins. After administration of the ganglionic blocker pentolinium (5 mg/kg i.v.), the angiotensin II infusion (0.3 µg/kg/min) is started. As soon as the blood pressure values have reached a stable plateau, the test substances are either administered intravenously or orally as a suspension or solution in 0.5% Tylose. The blood pressure changes under the action of the substance are given in the table as mean values ±SEM.

Determination of the antihypertensive activity in conscious hypertensive rats

The oral antihypertensive activity of the compounds according to the invention was tested in conscious rats using surgically induced unilateral renal artery stenosis. To do this, the right renal artery was constricted with a silver clip of 0.18 mm internal width. In this form of hypertension, the plasma renin activity is increased in the first six weeks after intervention. The arterial blood pressure of these animals was measured in a blood-free manner at defined time intervals after substance administration using the "tail cuff". The substances to be tested were suspended in a Tylose suspension and administered intragastrally ("orally") in various doses by stomach tube. The compounds according to the invention reduce the arterial blood pressure of the hypertensive rats at a clinically relevant dose.

Additionally, the compounds according to the invention inhibit the specific binding of radioactive angiotensin II in a concentration-dependent manner.

Interaction of the compounds according to the invention with the angiotensin II receptor in membrane fractions of the adrenal gland cortex (bovine)

Bovine adrenal gland cortices (AGC), which have been freshly removed and carefully freed from gland medulla, are comminuted in sucrose solution (0.32 M) with the aid of an Ultra-Turrax (Janke & Kunkel, Staufen i.B.) to give a coarse membrane homogenate and partially purified in two centrifugation steps to give membrane fractions. The receptor binding investigations are carried out on partially purified membrane fractions of bovine AGC using radioactive angiotensin II in an assay volume of 0.25 ml, which specifically contains the partially purified membranes (50-80 µg), $^3H$-angiotensin II (3-5 nM), test buffer solution (50 mMTris, pH 7.2, 5 mM $MgCl_2$) and the substances to be investigated. After an incubation time of 60 min at room temperature, the unbound radioactivity of the samples is separated by means of moistened glass fibre filters (Whatman GF/C) and the bound radioactivity is measured spectrophotometrically in a scintillation cocktail after washing the protein with ice-cold buffer solution (50 mM Tris/HCl, pH 7.4, 5% PEG 6000). The analysis of the raw data was carried out using computer programs to give $K_i$ or $IC_{50}$ values ($K_i$: $IC_{50}$ values corrected for the radioactivity used; $IC_{50}$ values: concentration at which the substance to be investigated causes a 50% inhibition of the specific binding of the radioligand).

TABLE B

| Ex. No. | Ki [nM] |
|---|---|
| 30 | 340 |
| 31 | 310 |
| 36 | 150 |
| 37 | 190 |

Investigation of the inhibition of the proliferation of smooth muscle cells by the compounds according to the invention To determine the antiproliferative action of the compounds, smooth muscle cells are used which are obtained from aortas of pigs by the media explant technique [R.Ross, J. Cell. Biol. 50, 172, 1971]. The cells are inoculated into suitable culture dishes, as a rule 96-hole plates, and cultured in 5% $CO_2$ at 37° C. for 2–3 days in medium 199 containing 7.5% FCS and 7.5% NCS, 2 mmol L-glutamine and 15 mmol HEPES, pH 7.4. The cells are then synchronised by withdrawal of serum for 2–3 days and then stimulated into growth with serum or other factors. Test compounds are simultaneously added. After 16–20 hours, 1 $\mu$Ci $^3$H-thymidine is added and after a further 4 hours the incorporation of this substance into the TCA-precipitatable DNA of the cells is determined.

To determine the $IC_{50}$ values, the active compound concentration is calculated which on sequential dilution of the active compound causes half-maximal inhibition of the thymidine incorporation produced by 1% FCS.

TABLE C

| Ex. No. | Inhibition [%] at $10^{-6}$ M |
|---|---|
| 18 | 90 |
| 39 | 59 |
| 40 | 57 |

The new active compounds can be converted in a known manner into the customary formulations, such as tablets, coated tablets, pills, granules, aerosols, syrups, emulsions, suspensions and solutions, using inert, non-toxic, pharmaceutically suitable excipients or solvents. In this case, the therapeutically active compound should in each case be present in a concentration of about 0..5 to 90% by weight of the total mixture, i.e. in amounts which are sufficient in order to achieve the dosage range indicated.

The formulations are prepared, for example, by extending the active compounds with solvents and/or excipients, if appropriate using emulsifiers and/or dispersants, where, for example, in the case of the use of water as a diluent, organic solvents can optionally be used as auxiliary solvents.

Administration is carried out in a customary manner, preferably orally or parenterally, in particular perlingually or intravenously.

In the case of parenteral administration, solutions of the active compound can be employed using suitable liquid excipient materials.

In general, it has proven advantageous in the case of intravenous administration to administer amounts of about 0.001 to 1 mg/kg, preferably about 0.01 to 0.5 mg/kg, of bodyweight to achieve effective results, and in the case of oral administration the dose is about 0.01 to 20 mg/kg, preferably about 0.1 to 10 mg/kg, of body weight.

In spite of this, it may sometimes be necessary to deviate from the amounts mentioned, namely depending on the body weight or the type of application route, on individual behaviour towards the medicament, the manner of its formulation and the time or interval at which administration takes place. Thus, in some cases it may be adequate to manage with less than the abovementioned minimum amount, while in other cases the upper limit mentioned must be exceeded. In the case of the administration of relatively large amounts, it may be advisable to divide these into several individual doses over the course of the day.

| Solvent mixtures | |
|---|---|
| A = Petroleum ether:ethyl acetate = | 5:1 |
| B = Dichloromethane:methanol = | 50:1 |
| C = Petroleum ether:ethyl acetate = | 10:1 |
| D = Petroleum ether:ethyl acetate = | 2:1 |
| E = Petroleum ether:ethyl acetate = | 1:1 |
| F = Dichloromethane:methanol = | 20:1 |
| G = Dichloramethane:methanol = | 10:1 |
| H = Dichloromethane:methanol = | 5:1 |
| I = Dichloromethane:methanol = | 30:1 |
| J = Petroleum ether:ether = | 20:1 |
| K = Petroleum ether:ethyl acetate = | 20:1 |

Starting Compounds

Example I

Methyl 2-cyclopentyl-2-(4-methylphenyl)acetate

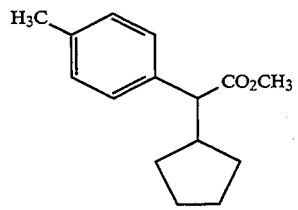

At 0° C., a suspension of 5.68 g (189 mmol) of sodium hydride (80% strength, stabilised with paraffin) is introduced into 200 ml of dimethylformamide with exclusion of moisture and the suspension is treated dropwise with stirring with 30.96 g (189 mmol) of methyl 2-(4methylphenyl)acetate [synthesis: J. B. Lambert, H. W. Mark and E. S. Magyar, J. Am. Chem. Soc. 99, 3059 (1977)] and 28.10 g (189 mmol) of cyclopentyl bromide in 300 ml of dimethylformamide. The mixture is stirred at 20° C. for 18 h and most of the solvent is evaporated in vacuo. The crude mixture is taken up with water and extracted several times with ether. After drying of the combined organic phases with sodium sulphate, the mixture is concentrated in vacuo and 41.04 g (177 mmol) of product are obtained. $R_f$=0.57 (c)

Example II

Methyl 2-cyclopentyl-2-(3-methylphenyl)acetate

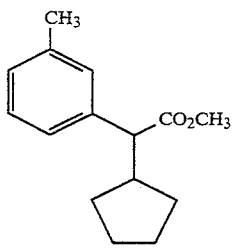

The title compound is prepared in analogy to the procedure of Example I. $R_f=0.56$(C)

Example III 4-(1-Cyclopentyl-2-hydroxy-ethyl)-toluene

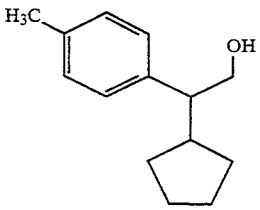

40.98 g (176 mmol) of the compound from Example I are dissolved in 400 ml of tetrahydrofuran and treated at 0° C. with exclusion of moisture with 3.35 g (88 mmol) of lithium aluminium hydride. The reaction mixture is stirred at 20° C. for 1.5 h and, if starting material is still present (TLC checking: C), reacted with a further 3.35 g (88 mmol) of lithium aluminium hydride. After 18 h at 20° C., the mixture is hydrolysed cautiously with water, acidified with 2 M sulphuric acid and extracted several times with ether, and the combined organic extracts are dried with sodium sulphate. Evaporation of the solvent in vacuo yields 33.7 g (165mmol) of product. $R_f=0.16$ (C)

Example IV 3-(1-Cyclopentyl-2-hydroxy-ethyl) to toluene

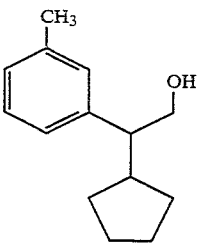

The title compound is prepared in analogy to the procedure of Example III. $R_f=0.19$(C)

Example V

2-Cyclopentyl-2-(4-methylphenyl)-ethyl methanesulphonate

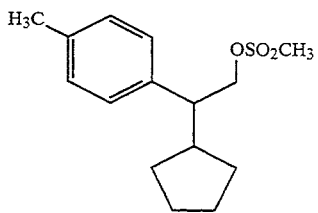

26.21 g (128 mmol) of the compound from Example III are dissolved in dichloromethane (200 ml) together with 12.98 g (128 mmol) of triethylamine and the mixture is reacted with 14.70 g (128 mmol) of methanesulphonyl chloride at 0° C. After 2.5 h at this temperature, the mixture is treated with 1 M sulphuric acid, the phases are separated and the organic solution is re-extracted once each with 1 M sulphuric acid, water, aqueous sodium hydrogen carbonate solution, and a further time with water. The organic extract is dried with sodium sulphate and after evaporation of the solvent yields 29.79 g (105 mmol) of product. $R_f=0.72$ (dichloromethane)

Example VI

2-Cyclopentyl-2-(3-methylphenyl)ethyl methanesulphonate

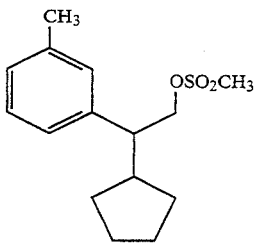

The title compound is obtained in analogy to the procedure of Example V. $R_f=0.76$ (dichloromethane)

Example VII

3-Cyclopentyl-3-(4-methylphenyl)-propionitrile

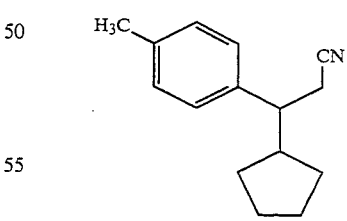

19.6 g (69 mmol) of the compound from Example V are reacted with 3.92 g (83mmol) of sodium cyanide in 400 ml of dimethyl sulphoxide at 90° C. After 45 minutes at this temperature, the mixture is diluted with ether, washed with iron chloride solution and water, the organic phase is dried with sodium sulphate and the solvent is evaporated. The crude product obtained is purified by chromatography on silica gel 60 (Merck, petroleum ether: ethyl acetate=100:1 to 50:1). Yield:

10.4 g (49 mmol) R$_f$=0.23 (petroleum ether: ethyl acetate=20:1).

Example VIII

3-Cyc lopentyl-3-(3-methylphenyl )propionitrile

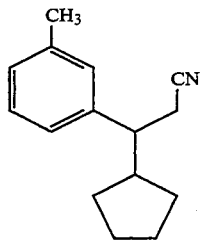

The title compound is prepared in analogy to the procedure of Example VII. R$_f$=0.33 (C)

Example IX 5-(2-Cyclopentyl )-2-(4-methylphenyl )-ethyl )tetrazole

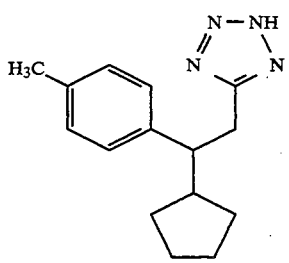

1.36 g (6.4 mmol ) of the compound from Example VII are reacted with 2.07 g (31.9 mmol ) of sodium azide and 4.39 g (31.9 mmol) of triethylammonium chloride in 20 ml of dimethylformamide at reflux temperature. If the reaction has not proceeded to completion after 1 d, (TLC checking: F), a further 1.04 g (15.9 mmol) of sodium azide and 2.20 g (15.9 mmol) of triethylammoniumchloride are added and the mixture is heated under reflux for a further 24 h. For working-up, it is poured into 1 M hydrochloric acid/ether, the organic phase is dried with sodium sulphate and the solvent is evaporated. The crude product obtained is stirred with dichloromethane, filtered off with suction and freed from residual solvent in Vacuo. Yield: 1.15 g (4.5 mmol) R$_f$=0.44 (F)

Example X 5-(2-Cyclopentyl )-2-(3-methylphenyl )-ethyl )-tetrazole

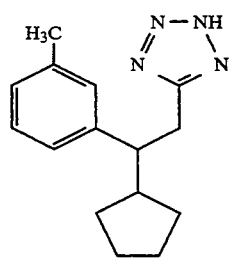

The title compound is obtained in analogy to the procedure of Example IX. R$_f$=0.40 (F)

Example XI 5-(2-Cyc lopentyl-2-(4-methylphenyl ) -ethyl ) -2-triphenyl-methyl-tetrazole

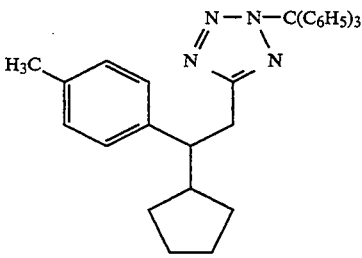

1.10 g (4.3 mmol) of the compound from Example IX are dissolved in 16 ml of dichloromethane and the mixture is reacted at 20° C. with 1.32 g (4.7 mmol) of triphenylchloromethane and 0.56 g (5.6 mmol) of triethylamine. After 6 h, the mixture is treated with 1 M aqueous citric acid solution and extracted with ether. The organic phases are dried with sodium sulphate and finally evaporated in a high vacuum. Yield: 2.3 g (4.3 mmol) R$_f$=0.71 ( petroleum ether: ethyl acetate =5: 1 ).

Example XII 5-(2-Cyclopentyl-2-(3-methylphenyl ) -ethyl ) -2-triphenyl-methyl-tetrazole

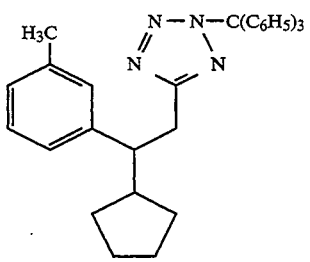

The title compound is prepared in analogy to the procedure of Example XI. R$_f$=0.85 (dichloromethane)

Example XIII 5-(2-Cyclopentyl ) -2-(4-bromomethylphenyl ) -ethyl ) -2-triphenylmethyl-tetrazole

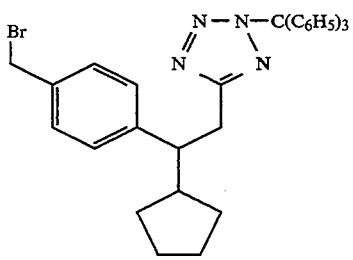

2.28 g (4.3 mmol) of the compound from Example XI are dissolved in 30 ml of tetrachloromethane, and the solution is treated with 0.77 g (4.3 mmol) of N-bromosuccinimide and 0.1 g of azobisisobutyronitrile and heated under reflux for 6 h. After cooling, the resulting precipitate is filtered off with suction, the filtrate is evaporated and the residue is reacted further as crude product. Yield: 2.6 g (4.2 mmol) $R_f=0.57$ (A)

The compounds shown in Table I are prepared in analogy to the procedure of Example XIII:

TABLE I

| Ex. No. | | $R_f$ (mobile phase) |
|---|---|---|
| XIV | | 0.08 (I) |
| XV | | 0.32 (C) |
| XVI | | 0.32 (K) |
| XVII | | 0.40 (K) |
| XVIII | | 0.51 (C) |
| XIX | | 0.64 (C) |

TABLE I-continued

| Ex. No. | | $R_f$ (mobile phase) |
|---|---|---|
| XX | | 0.54 (C) |

Example XXI

3-Cyclopentyl-3-(4-methylphenyl)propionic acid

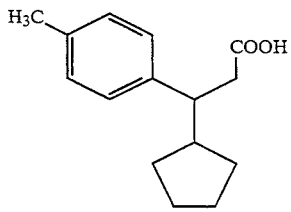

6.10 g (28.6 mmol) of the compound from Example VII are dissolved in 40 ml of ethanol and treated with 60 ml of 1 M aqueous sodium hydroxide solution. The mixture is heated under reflux for 2 d, adjusted to pH=2 with 2 M hydrochloric acid after cooling and extracted several times with ether. The organic phases dried using sodium sulphate are evaporated and the crude product thus obtained is purified by chromatography on silica gel 60 (Merck, petroleum ether: ethyl acetate=5:1, 2:1, 1:1 and finally 1:2). 2.74 g (11.8 mmol) of the above-mentioned product ($R_f=0.72$/E) and 2.03 g (8.8 mmol) of 3-cyclopentyl-3-(4-methylphenyl)propionamide ($R_f=0.14$/E) are obtained.

Example XXII

3-Cyclopentyl-3-(3-methylphenyl) propionic acid

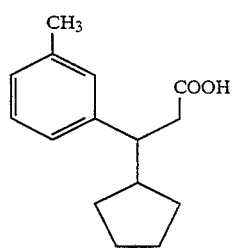

The title compound is prepared in analogy to the procedure of Example XXI. $R_f=0.77$ (E)

Example XXIII

3-Cyclopentyl-3-(4-methylphenyl) propionyl chloride

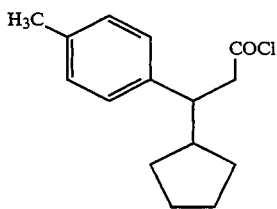

4.34 g (18.7 mmol) of the compound from Example XXI are reacted under reflux in 100 ml of toluene with 4.98 g (39.2 mmol) of oxalyl chloride. After 2 h, the solvent is evaporated off with excess reagent, the crude product is taken up again in toluene and the mixture is evaporated once more. To remove the reagent completely, this process is repeated several times if necessary. The crude product is further reacted without additional purification.

Example XXIV

3-Cyclopentyl-3-(3-methylphenyl)propionyl chloride

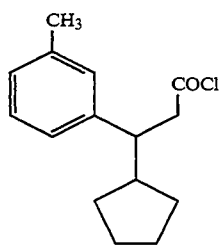

The title compound is prepared in analogy to the procedure of Example XXIII.

Example XXV tert-Butyl 3-cyclopentyl-3-(4-methylphenyl)propionate

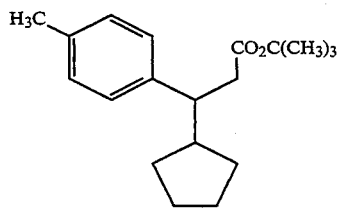

The crude product from Example XXIII is dissolved in 40 ml of tetrahydrofuran and treated cautiously at 20° C. in portions with a total of 2.1 g (18.7 mmol) of potassium tert-butoxide. The mixture is stirred for 2 h, poured into saturated, aqueous sodium hydrogen carbonate solution and extracted with ether. The collected ethereal phases are dried with sodium sulphate and concentrated on a rotary evaporator. Residual solvent is removed in a high vacuum. Yield: 5.21 g (18.1 mmol) $R_f$=0.80 (A)

Example XXVI tert-Butyl 3-cyclopentyl-3-(3-methylphenyl)propionate

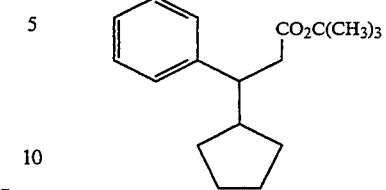

The title compound is prepared in analogy to the procedure of Example XXVI. $R_f$=0.47 (petroleum ether: ethyl acetate=20:1).

Example XXVII tert-Butyl 3-(3-methylphenyl)-3-phenyl-proPionate

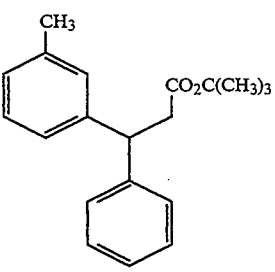

The title compound is prepared in analogy to the procedure of Example XXV. $R_f$=0.67 (C).

Example XXVIII 4-(2-Azido-1-cyclopentyl-ethyl)-toluene

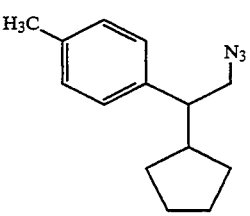

500 mg (1.8 mmol) of the compound from Example V are dissolved in 10 ml of dimethyl sulphoxide and reacted at 90° C. with 140 mg (2.1mmol) of sodium azide. After 1.5 h, the mixture is taken up in 150 ml of ether and 150 ml of water and re-extracted several times. The organic phases are dried with sodium sulphate and evaporated. Yield: 370 mg(1.6 mmol) $R_f$=0.69 ( petroleum ether: ethyl acetate =20:1 )

Example XXIX tert-Butyl (E,Z)-3-(4-methylphenyl ) -3-phenyl-propenoate

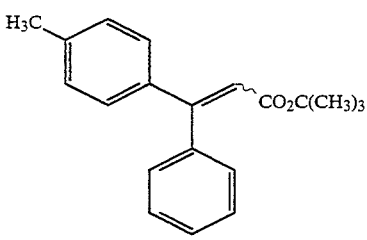

20.0 g (102 mmol) of 4-methylbenzophenone (commercially available from Aldrich) are dissolved in 200 ml of toluene, and the solution is treated with 6.95 g (231 mmol) of sodium hydride (80% strength, stabilised with paraffin) and heated to 80° C. with stirring. A mixture of 112 g (964 mmol) of tert-butyl acetate (commercially available from Aldrich) and 13.73 g (185 mmol) of tert-butanol is added dropwise at this temperature and the reaction mixture is then stirred for 30 h at 90° C. After cooling, 200 ml of saturated aqueous sodium hydrogen carbonate solution are added and the mixture is extracted several times with ether. The organic phase is dried with sodium sulphate and evaporated. The crude product is isolated by chromatography (silica gel 60, Merck, petroleum ether dichloromethane =10: 1 ) . Yield: 24.9 g (85mmol) $R_f$=0.67 (C)

Example XXX tert-Butyl 3-(4-methylphenyl ) -3-phenyl-propionate

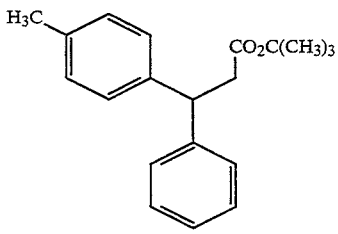

6.0 g (20.5 retool) of the compound from Example XXIX are dissolved in 200 ml of methanol and the mixture is reacted at 20 ° C. with 5.0 g (205 mmol) of magnesium turnings. After 3 h, the precipitate is filtered off with suction, the filtrate is evaporated, the residue is taken up with water and the mixture is extracted with ether. The organic phase is dried with sodium sulphate and evaporated. Yield: 5.8 g (19.6 mmol) $R_f$=0.81 (C)

Example XXXI

N, N-Diethyl-3-(3-methylphenyl )-3-phenyl-propionamide

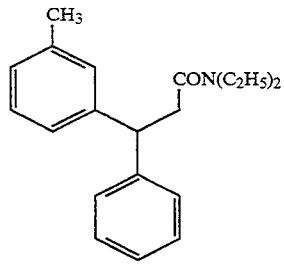

The title compound is prepared in analogy to the procedure of Example XXX. $R_f$=0.65 (E)

Example XXXII and Example XXXIII

N, N-Diethyl-3-hydroxy-3-(3-methylphenyl ) -3-phenylpropionamide (XXXII) and (E,Z)-N,N-diethyl-3-(3-methylphenyl)-3-phenyl-propenamide (XXXIII)

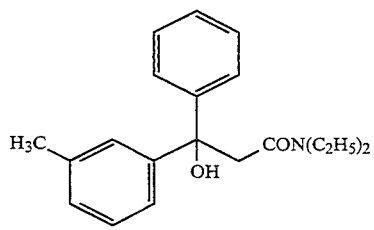

(XXXII)

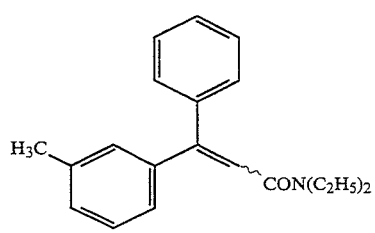

(XXXIII)

150 ml of 2 M isopropylmagnesium chloride solution in ether are treated at 0° C. with 44.8 g (612 mmol) of diethylamine and heated under reflux for 30 minutes, again cooled to —5° C. and stirred with a mixture of 20.0 g (102 mmol) of 3-methylbenzophenone (commercially available from Aldrich) and 13.75 g (102 mmol) of tert-butyl acetate (commercially available from Aldrich) in 100 ml of ether. The mixture is heated under reflux for 3 h and, after cooling, poured into ice-water, acidified. with 10 sulphuric acid and extracted several times with ether. After drying the organic phase with sodium sulphate, the solvent is evaporated. Chromatographic separation of the product mixture (silica gel 60, Merck, C) yields 11.3 g (40mmol of the compound XXXII and 6.5 g (23mmol) of the compound XXXIII. $R_f$=0.57 (A) XXXIZ $R_f$=0.11 (A) XXXIII Example XXXIV 3-(3-Methylphenyl)-3-phenyl-propionic acid

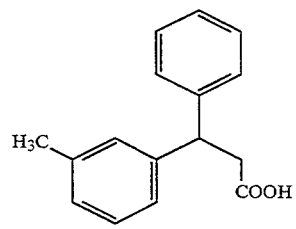

10.1 g (35.8mmol) of the compound from Example XXXII are dissolved in 200 ml of dichloromethane, treated cautiously with 33.27 g (286.2 mmol) of triethylsilane and 130.5 g (1.14 mol) of trifluoroacetic acid and stirred at 20° C. for 4 h. Water is added and the phases are separated. The organic solution is concentrated on a rotary evaporator and the residue is taken up in 1 M sodiumhydroxide solution (pH=12). The alkaline aqueous phase is washed with dichloromethane and adjusted to pH=2 with hydrochloric acid and the precipitate obtained is filtered off with suction and washed with water. After drying in a high vacuum over phosphorus pentoxide and sodium hydroxide, 6.6 g (27.5 mmol) of product are obtained. $R_f=0.28$ (F)

Example XXXV

N-(2-(4-Tolyl ) -2-cyclopentyl-ethyl ) -methanesulphonyl chloride

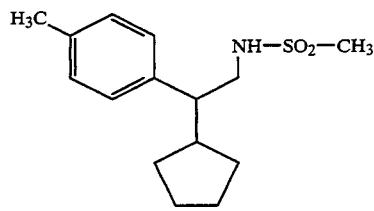

The title compound is obtained in analogy to the procedure of Example 45, which is given later. Yield: 0.065 g (0.2 mmol ) $R_f=0.79$ (I)

The compounds shown in Table I I are prepared in analogy to the preparation procedure of Example XXXV:

TABLE II

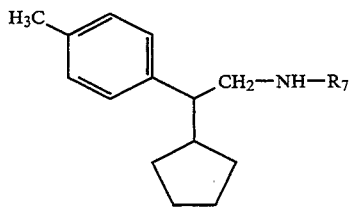

| Ex. No. | $R^7$ | $R_f$(mobile phase) |
|---|---|---|
| XXXVI | —CO—C6H4—CH3 | 0.87 (I) |
| XXXVII | —CO—CH3 | 0.32 (I) |
| XXXVIII | —SO2—CH2—C6H5 | 0.93 (I) |

TABLE II-continued

| Ex. No. | $R^7$ | $R_f$(mobile phase) |
|---|---|---|
| XXXIX | —SO2—CF3 | 0.93 (I) |

Preparation Examples

Example 1

5-(2-[4-(2-Butyl-4-chloro-5-formyl-imidazol-1-ylmethyl )phenyl ]-2-cyclopentyl-ethyl )-2-triphenylmethyltetrazole

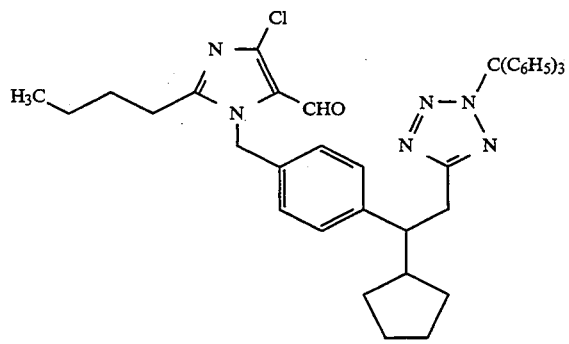

0.80 g (4.3 mmol) of 2-butyl-4-chloro-imidazole-4carbaldehyde [Synthesis: EP 324,377]are dissolved in 10 ml of dimethylformamide and deprotonated at 0° C. using 129 mg (4.3 mmol) of sodium hydride (80% strength, stabilised with paraffin). 15 minutes after evolution of gas is complete, 2.64 g (4.3 mmol) of the compound from Example XIII are added dropwise in 3 ml of dimethylformamide, and the reaction mixture is stirred at 20° C. for 1 d. Addition of water follows extraction with ether and drying of the organic phase with sodium sulphate. The residue obtained on evaporation of the ether solution is purified by chromatography on silica gel 60 (Merck, eluent C) and yields 1.80 g (2.5 mmol) of product. $R_f=0.52$ (A)

The examples shown in Table 1 are prepared in analogy to the procedure of Example 1:

TABLE 1

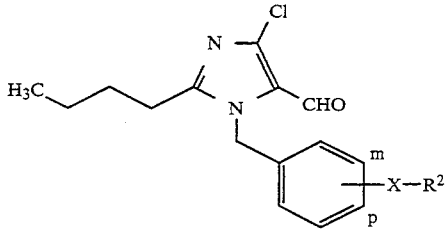

| Ex. No. | Position | X | R⁵ | R² | $R_f$ (mobile phase) |
|---|---|---|---|---|---|
| 2 | m | —CHR⁵—CH₂— | cyclopentyl |  | 0.55 (A) |
| 3 | p | —CHR⁵—CH₂— | cyclopentyl | —CO₂C(CH₃)₃ | 0.25 (A) |
| 4 | m | —CHR⁵—CH₂— | cyclopentyl | —CO₂C(CH₃)₃ | 0.52 (B) |
| 5 | p | —CHR⁵—CH₂— | cyclopentyl | —N₃ | 0.09 (C) |
| 6 | p | (E)—CR⁵=CH— | phenyl | —CO₂C(CH₃)₃ | 0.63 (D) |
| 7 | p | (Z)—CR⁵=CH— | phenyl | —CO₂C(CH₃)₃ | 0.59 (D) |
| 8 | p | —CHR⁵—CH₂— | phenyl | —CO₂C(CH₃)₃ | 0.32 (A) |
| 9 | m | —CHR⁵—CH₂— | phenyl | —CO₂C(CH₃)₃ | 0.40 (A) |

Example 10

5-(2- [4-(2-Butyl-4-chl oro-5-hydroxymethyl- imidazo 1-1-ylmethyl ) -phenyl ]-2-cyc lopentyl-ethyl ) -2-tri-phenylmethyltetrazole

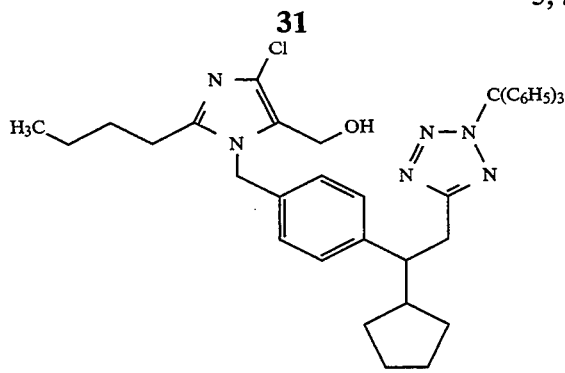

530 g (0.74 mmol) of the compound from Example 1 are reacted at 20° C. with 27 mg(0.70 mmol) of sodium borohydride in 2 ml of methanol. After 4 h, the mixture is evaporated and the crude product is purified by chromatography on silica gel 60 (Merck, eluent D). Yield: 392 mg (0.54 mmol) $R_f$=0.17 (D)

The examples shown in Table 2 are prepared in analogy to the procedure of Example 10:

TABLE 2

| Ex. No. | Position | X | $R^5$ | $R^2$ | $R_f$ (mobile phase) |
|---|---|---|---|---|---|
| 11 | m | —CHR⁵—CH₂— | cyclopentyl | $\begin{array}{c}C(C_6H_5)_3\\|\\N-N\\ \\\\ \diagdown\\N=N\end{array}$ tetrazole | 0.41 (E) |
| 12 | p | —CHR⁵—CH₂— | cyclopentyl | —CO₂C(CH₃)₃ | 0.71 (E) |
| 13 | p | —CHR⁵—CH₂— | cyclopentyl | —N₃ | 0.25 (F) |
| 14 | m | CHR⁵—CH₂— | cyclopentyl | —CO₂C(CH₃)₃ | 0.36 (F) |
| 15 | p | (E)—CR⁵=CH— | phenyl | —CO₂C(CH₃)₃ | 0.25 (D) |
| 16 | p | (Z)—CR⁵=CH— | phenyl | —CO₂C(CH₃)₃ | 0.21 (D) |
| 17 | m | —CHR⁵—CH₂— | phenyl | —CO₂C(CH₃)₃ | 0.54 (E) |
| 18 | p | —CHR⁵—CH₂— | phenyl | —CO₂C(CH₃)₃ | 0.26 (D) |

TABLE 2-continued

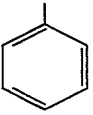

| Ex. No. | Position | X | R⁵ | R² | R$_f$(mobile phase) |
|---|---|---|---|---|---|
| 19 | p | (E)—CR⁵=CH— | phenyl | —CO—NH—CH(C₆H₅)—CH₂OH | 0.16 (F) |
| 20 | p | (Z)—CR⁵=CH— | phenyl | —CO—NH—CH(C₆H₅)—CH₂OH | 0.15 (F) |
| 21 | p | HR⁵—CH₂— | phenyl | —CO—NH—SO₂—C₆H₄—CH₃ | 0.44 (F) |

Example 22

5-(2- [4-(2-Butyl-4-chloro-5-formyl-imidazol-1-ylmethyl) phenyl ]-2-cyclopentyl-ethyl ) -tetrazole

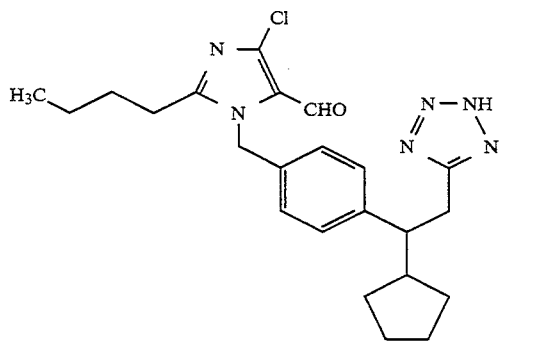

134 mg (0.19 mmol) of the compound from Example 1 are reacted with 0.8 ml of trifluoroacetic acid and 0.8 ml of water in 2 ml of tetrahydrofuran. After 2 h at 20° C., the mixture is adjusted to pH=13 with 2 M sodium hydroxide solution, the aqueous phase is separated off and residual organic solvent is stripped off from the aqueous phase on a rotary evaporator. At 0° C., the mixture is adjusted to pH=1.6 with 2 M hydrochloric acid, the precipitate obtained is filtered off with suction and washed with water, and the product is dried in a high vacuum over phosphorus pentoxide and sodium hydroxide. Yield: 51 mg (0.11 mmol) R$_f$=0.47 (F)

The examples shown in Table 3 are prepared in analogy to the procedure of Example 22:

TABLE 3

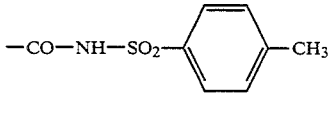

| Ex. No. | Position | D | R$_f$(mobile phase) |
|---|---|---|---|
| 23 | p | —CH₂OH | 0.04 (F) |
| 24 | m | —CHO | 0.20 (F) |
| 25 | m | —CH₂OH | 0.06 (F) |

Example 26

3-[4 (2 -Butyl-4-chloro-5-hydroxymethyl- imidazo 1-1-ylmethyl )phenyl ]-3-cyclopentyl-propionic acid

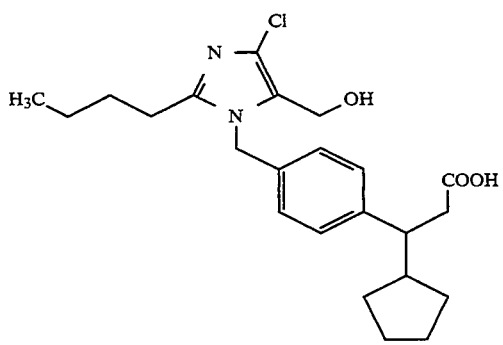

0.66 g (1.4mmol) of tert-butyl 3-[4-(2-butyl-4-chloro-5-hydroxymethyl-imidazol-1-yl-methyl)-phen pentyl-propionate are dissolved in 20 ml of 1,4-dioxane and treated with 2 ml of concentrated hydrochloric acid. The mixture is stirred at 20° C. for 20 h and diluted with 2 M hydrochloric acid, and the phases are separated. The organic phase is evaporated, the residue is taken up in aqueous sodium hydroxide solution (pH=11) and the mixture is washed with ether. The residual organic solvent of the aqueous phase is then removed in vacuo on a rotary evaporator and the product is precipitated at 0° C. with 2 M hydrochloric acid at pH=2, filtered off with suction, washed with water .and dried in a high vacuum over sodium hydroxide and phosphorus pentoxide. Yield: 0.46 g (1.1 mmol) $R_f$=0.16 (F)

The examples shown in Table 4 are prepared in analogy to the procedure of Example 26:

TABLE 4

| Ex. No. | Position | X | $R^5$ | D | $R_f$ (mobile phase) |
|---|---|---|---|---|---|
| 27 | m | —CHR$^5$—CH$_2$— | cyclopentyl | —CHO | 0.29 (F) |
| 28 | m | —CHR$^5$—CH$_2$— | cyclopentyl | —CH$_2$OH | 0.17 (G) |
| 29 | p | (E)—CR$^5$=CH— | phenyl | —CH$_2$OH | 0.56 (H) |
| 30 | p | (Z)—CR$^5$=CH— | phenyl | —CH$_2$OH | 0.56 (H) |
| 31 | p | (E)—CR$^5$=CH— | phenyl | —CHO | 0.59 (G) |
| 32 | m | —CHR$^5$—CH$_2$— | phenyl | —CHO | 0.28 (G) |
| 33 | m | —CHR$^5$—CH$_2$— | phenyl | —CH$_2$OH | 0.18 (G) |

TABLE 4-continued

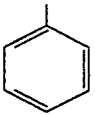

| Ex. No. | Position | X | R⁵ | D | R_f (mobile phase) |
|---|---|---|---|---|---|
| 34 | p | (Z)—CR⁵=CH— | phenyl | CHO | 0.54 (G) |
| 35 | p | —CHR⁵—CH₂— | phenyl | CHO | 0.19 (F) |
| 36 | p | —CHR⁵—CH₂— | phenyl | CH₂OH | 0.43 (G) |
| 37 | p | —CHR⁵—CH₂— | cyclopentyl | CHO | 0.40 (F) |

Example 38

N-(4-Tolylsulphonyl)-3-[4-(2-butyl-4-chloro-5-formyl-imidazol-1-yl-methyl) phenyl]-3-phenyl-propionamide

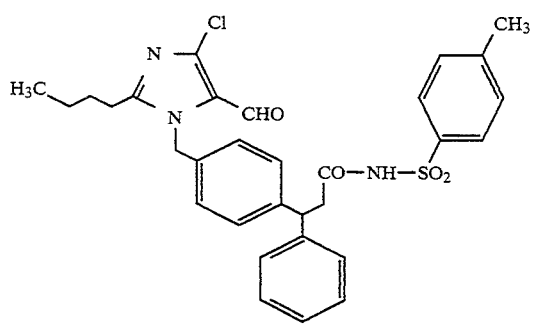

0.30 g (0.7 mmol) of 3-[4-(2-butyl-4-chloro-5-formyl-imidazol-1-yl-methyl)-phenyl]-3phenyl-propionic acid are reacted at —20° C. in 15 ml of tetrahydrofuran with 60 μl (0.77 mmol) of methanesulphonyl chloride and 428 μl (3.10 mmol) of triethylamine. After the mixture has been stirred at —20° C. for 2 h, 148 mg (0.85 mmol) iof 4-toluenesulphonamide and 343 mg (2.82 mmol) of 4-(N,N-dimethylamino)pyridine are added. The reaction temperature rises to 20° C. after removal of the cooling bath, and the mixture is stirred for 1 d. Aqueous sodium hydrogen carbonate solution is then added and the mixture is extracted with ether. The organic solution is dried with Sodium sulphate and evaporated, and the residue is purified by chromatography on silica gel 60 (Merck, dichloromethane: methanol=100:1). Yield: 0.24 g (0.4 mmol) R_f=0.62 (F)

The examples shown in Table 5 are prepared in analogy to the procedure of Example 38:

TABLE 5

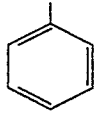

| Ex. No. | Position | X | R⁵ | R_f (mobile phase) |
|---|---|---|---|---|
| 39 | p | (E)—CR⁵=CH— | phenyl | 0.66 (E) |
| 40 | p | (Z)—CR⁵=CH— | phenyl | 0.56 (E) |

Example 41

N,L-Phenylglycinol-3-[4-(2-butyl-4-chloro-5-formyl-imidazol-1-yl-methyl)-phenyl ]-3-phenyl-propionamide

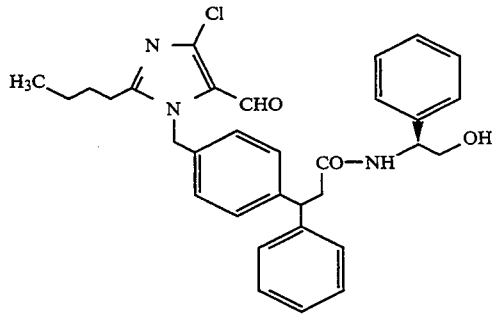

0.30 g (0.7 mmol) of 3-[4-(2-butyl-4-chloro-5-formylimidazo 1-yl-methyl )-phenyl ]-3-phenyl-propionic acid are reacted at —20° C. in 15 ml of tetrahydrofuran with 60 μl (0.77 mmol) of methanesulphonyl chloride and 428 μl (3.10 mmol) of triethylamine. After stirring at —20° C. for a period of 2 h, 0.12 g (0.84 mmol) of L-phenylglycinol and 34.3 mg (2.82 mmol) of 4-(N,N-dimethylamino)pyridine are added and the mixture is stirred for 20 h while warming to 20° C. The mixture is adjusted to pH=9 with aqueous sodium hydrogen carbonate solution and extracted with ether. The organic phase is dried with sodium sulphate and evaporated, and the residue is purified by chroma-tography on silica gel 60 (Merck, dichloromethane: methanol=100: 1 ) . Yield: 0.12 g (0.2 mmol) $R_f$=0.62 (F)

The compounds shown in Table 6 are prepared in analogy to the procedure of Example 41:

TABLE 6

| Ex. No. | Position | X | $R^5$ | D | $R_f$ (mobile phase) |
|---|---|---|---|---|---|
| 42 | p | (E)—$CR^5$=CH— | | CHO | 0.79 (G) |
| | | | | (phenyl) | |
| 43 | p | (Z)—$CR^5$=CH— | | CHO | 0.68 (G) |
| | | | | (phenyl) | |

Example 44

1-(4-(2-Amino-1-cyclopentyl-ethyl ) phenyl-methyl ) -2-butyl-5-hydroxy-methyl-imidazole

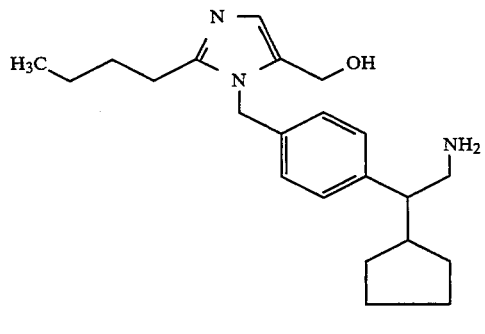

1.21 g (2.9 mmol) of 1-(4-(2-azido-1-cyclopentyl-ethyl)phenyl-methyl)-2-butyl-4-chloro-5-hydroxymethyl-imidazole are stirred in 15 ml of methanol at 20° C. with 1.2 g of palladium (10% on animal charcoal) and a hydrogen atmosphere. After 3 h, the catalystis filtered off and the filtrate is evaporated - finally in a high vacuum. Yield: 1.07 g (2.7 mmol) of product, which is processed in crude form $R_f$=0.57 (dichloromethane: methanol=2:1)

Example 45

1- [4-(2-Cyclopentyl-1-(N-methylsulphonyl-amino) ethyl)-phenyl-methyl]-2 -butyl -5-hydroxymethyl-imidazole

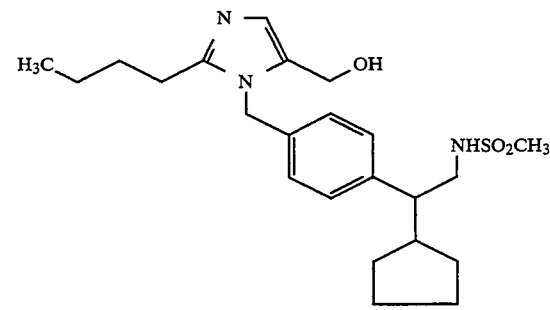

390 mg (1.0 mmol) of the compound from Example 44 are dissolved in 4 ml of dichloromethane and reacted with ice-cooling with 0.14 ml (1.0 mmol) of triethylamine and 0.08 ml (1.00 mmol) of methanesulphonyl chloride. After addition is complete, the mixture is stirred for 4 h and then extracted with 1 M sulphuric acid and ether. The organic phase is dried with sodium sulphate and evaporated, and the residue is purified by chromatography on silica gel 60 (Merck, dichloromethane: methanol 50:1, 20:1, 1:1 to methanol). Yield: 68 mg (0.2 mmol) $R_f$=0.03 (I)

The examples shown in Table 7 are prepared in analogy to the procedure of Example 45:

TABLE 7

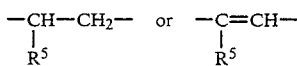

| Ex. No. | R⁷ | $R_f$ (mobile phase) |
|---|---|---|
| 46 | —SO₂—⟨C₆H₄⟩—CH₃ | 0.81 (I) |
| 47 | —CO—⟨C₆H₄⟩—CH₃ | 0.43 (I) |
| 48 | —CO—CH₃ | 0.01 (I) |
| 49 | —SO₂—CH₂—⟨C₆H₅⟩ | 0.85 (I) |
| 50 | —SO₂—CF₃ | 0.86 (I) |

We claim:

1. An imidazolyl-substituted phenylpropionic and cinnamic acid derivative of the formula

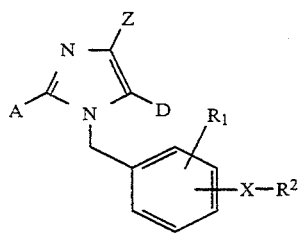

in which

A represents straight-chain or branched alkyl or alkenyl each having up to 8 carbon atoms, or represents cycloalkyl having 3 to 8 carbon atoms, Z represents hydrogen, halogen or perfluoroalkyl having up to 5 carbon atoms, D represents a group of the formula -CH₂OR³ or -CO-R⁴, in which R³ denotes hydrogen or Straight-chain or branched alkyl having up to 8 carbon atoms, R⁴ denotes hydrogen, hydroxyl or straight-chain or branched alkoxy having up to 8 carbon atoms, X represents a group of the formula —CH—CH₂—  or  —C=CH—
  |                |
  R⁵               R⁵ in which

R⁵ denotes cycloalkyl having 3 to 8 carbon atoms, or denotes phenyl, or denotes straight-chain or branched alkyl having up to 8 carbon atoms, which is optionally substituted by phenyl or cyclo-alkyl having 3 to 8 carbon atoms, R¹ represents hydrogen, halogen, nitro, hydroxyl, trifluoromethyl, trifluoromethoxy, straight-chain or branched alkyl, alkoxy or alkoxycarbonyl each having up to 6 carbon atoms, or cyano or carboxyl, R² represents

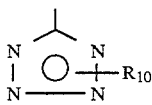

in which

R¹⁰ denotes hydrogen, straight-chain or branched alkyl having up to 6 carbon atoms or the triphenyl-methyl group or a salt thereof.

2. An imidazolyl-substituted phenylpropionic and cinnamic acid derivative according to claim 1 in which represents straight-chain or branched alkyl or alkenyl each having up to 6 carbon atoms, or represents cyclopropyl, cyclobutyl, cyclo-pentyl, cyclohexyl or cycloheptyl, Z represents hydrogen, fluorine, chlorine, bromine or perfluoroalkyl having up to 4 carbon atoms, D represents a group of the formula -CH₂OR³ or -CO-R⁴, in which R³ denotes hydrogen or straight-chain or branched alkyl having up to 6 carbon atoms, R⁴ denotes hydrogen, hydroxyl or straight-chain or branched alkoxy having up to 6 carbon atoms, X represents a group of the formula —CH—CH₂—  or  —C=CH—
  |                |
  R⁵               R⁵ in which

R⁵ denotes cyclopropyl, cyclopentyl, cyclohexyl, cycloheptyl or phenyl, or denotes straight-chain or branched alkyl having up to 6 carbon atoms, which is substituted by phenyl, cyclopropyl, cyclopentyl, cyclohexyl or cycloheptyl, R¹ represents hydrogen, fluorine, chlorine, bromine, trifluoromethyl, carboxyl or straight-chain or branched alkyl, alkoxy or alkoxycarbonyl each having up to 4 carbon atoms, R² represents

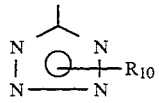

in which

3. An imidazolyl-substituted phenylpropionic and cinnamic acid derivative according to claim 1 in which A represents straight-chain or branched alkyl or alkenyl each having up to 4 carbon atoms, or represents cyclopropyl, cyclopentyl or cyclohexyl, Z represents hydrogen, fluorine, chlorine or perfluoroalkyl having up to 2 carbon atoms, D represents a group of the formula $-CH_2OR^3$ or $-CO-R^4$, in which $R^3$ denotes hydrogen or straight-chain or branched alkyl having up to 4 carbon atoms, $R^4$ denotes hydrogen, hydroxyl or straight-chain or branched alkoxy having up to 4 carbon atoms, X represents a group of the formula

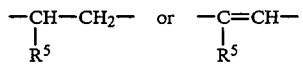

in which $R^5$ denotes cyclopentyl, cyclohexyl or phenyl, or denotes straight-chain or branched alkyl having up to 4 carbon atoms, which is optionally substituted by phenyl, cyclopentyl or cyclohexyl, $R^1$ represents hydrogen, fluorine, chlorine, bromine, trifluoromethyl, trifluoromethoxy or methyl, represents

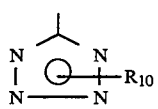

$R^{10}$ denotes hydrogen, methyl or the triphenylmethyl group of a salt thereof.

4. A compound according to claim 1 wheein such compound is 5-(2-[4-[2-butyl-4-chloro-5-formyl-imidazol-1-yl-methyl) -phenyl]-2-cyclopentyl-ethyl)-2-triphenylmethyl-tetrazole o9f the formula

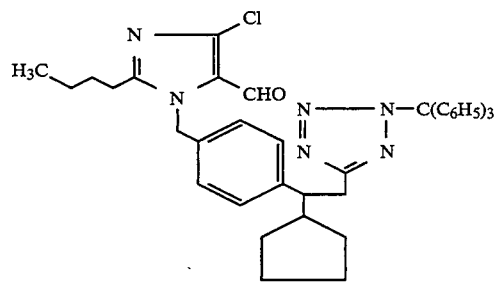

or a salt thereof.

5. A compound according to claim 1 wherein such compound is 5-(2-[4-(2-butyl-4-chloro-5-hydroxy methyl-imidazol-1-yl-methyl)phenyl]-2-cyciopentyl-ethyl)-2-triphenylmethy 1-tetrazol of the formula

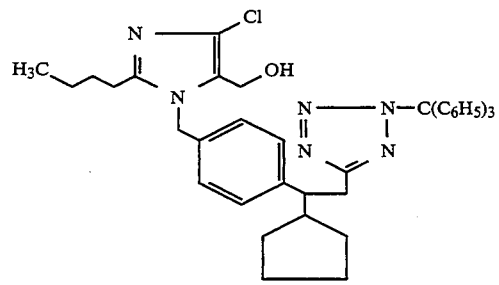

and salts thereof.

6. A compound according to claim 1 wherein such compound is 5-(2-[4-(2-butyl-4-chloro-5-fomyl-imidazol-1-yl-methyl)phenyl]-2-cyclo-pentyl-ethyl)tetraz

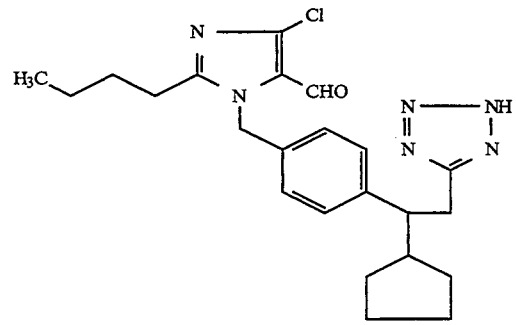

or a salt thereof.

7. A composition for the treatment of arterial hypertension and atherosclerosis comprising an amount effective therefor of a compound or salt thereof according to claim 1 and a pharmacologically acceptable diluent.

8. A method of treating arterial hypertension and atherosclerosis in a patient in need therefor which comprises administering an effective amount of a compound or a salt thereof according to claim 1.

* * * * *

UNITED STATES PATENT AND TRADEMARK OFFICE
CERTIFICATE OF CORRECTION

PATENT NO. : 5,414,008
DATED : May 9, 1995
INVENTOR(S) : Muller, et al.

It is certified that error appears in the above-indentified patent and that said Letters Patent is hereby corrected as shown below:

| | |
|---|---|
| Col. 42, line 32 | Before " represents " insert -- A -- |
| Col. 42, last line | After " in which " and under insert $R^{10}$ denotes hydrogen, straight-chain or branched alkyl having up to 4 carbon atoms or the triphenylmethyl group or a salt thereof. -- |
| Col. 43, line 42 | Before " represents " insert -- $R^2$ -- |
| Col. 43 line 51 | insert -- in which -- |
| Col. 43, line 56 | Delete " wheein " and substitute -- wherein -- |
| Col. 43, last line | Delete " 09f " and substitute -- of -- |
| Col. 44, line 18 | Delete " tetrazol " and substitute -- tetrazole -- |

UNITED STATES PATENT AND TRADEMARK OFFICE
CERTIFICATE OF CORRECTION

PATENT NO. : 5,414,008
DATED : May 9, 1995
INVENTOR(S) : Muller, et al.

It is certified that error appears in the above-indentified patent and that said Letters Patent is hereby corrected as shown below:

Col. 44, line 32.   Delete " and salts " and substitute -- or a salt --

Col. 44, lines 35-36   Delete " tetraz " and substitute -- tetrazole of the formula --

Signed and Sealed this

Fifteenth Day of August, 1995

Attest:

BRUCE LEHMAN

*Attesting Officer*     *Commissioner of Patents and Trademarks*